United States Patent [19]
Jacobs

[11] Patent Number: 5,312,350
[45] Date of Patent: May 17, 1994

[54] VEIN SPOTTER

[76] Inventor: Andrew Jacobs, 22 Hickory Rd., Short Hills, N.J. 07078

[21] Appl. No.: 983,240

[22] Filed: Nov. 30, 1992

[51] Int. Cl.$^5$ .............................................. A61M 5/00
[52] U.S. Cl. ................................... 604/116; 606/201; 606/204; 606/203
[58] Field of Search ............... 604/116; 128/384, 385, 128/DIG. 15; 119/106; 606/201, 202, 203, 204

[56] References Cited

U.S. PATENT DOCUMENTS

| | | | |
|---|---|---|---|
| 2,344,021 | 3/1944 | Bouziane | 606/201 |
| 3,167,072 | 1/1965 | Stone et al. | 604/116 |
| 3,570,496 | 3/1971 | Sachs | 606/203 |
| 4,243,028 | 1/1981 | Payana | 606/204 |
| 4,314,568 | 2/1982 | Loving | 604/116 |
| 4,479,495 | 10/1984 | Isaacson | 606/204 |
| 4,716,898 | 1/1988 | Chauve et al. | 606/204 |
| 5,078,728 | 1/1992 | Giarratano | 606/204 |

FOREIGN PATENT DOCUMENTS

| | | | |
|---|---|---|---|
| 3404528 | 8/1985 | Fed. Rep. of Germany | 606/204 |
| 0115789 | 5/1918 | United Kingdom | 606/203 |

*Primary Examiner*—John G. Weiss
*Attorney, Agent, or Firm*—Weingram & Zall

[57] ABSTRACT

The present invention relates to a vein spotter which consists of a flexible band which has a buckle attached to one end and a hook and pile Velcro type of fastener mounted on a first surface. A plurality of protrusion members are mounted on the second surface of the band. The buckle and the hook and pile fastener allow the flexible band to be formed into a loop encircling a limb with the protrusion members pushing into skin, displacing tissue into spaces formed between the projecting members and causing superficial veins to distend and become visible.

15 Claims, 3 Drawing Sheets

VEIN SPOTTER

BACKGROUND OF THE INVENTION

1. Field of the Invention

This invention relates to an improved vein spotter which facilitates the distention and stabilization of superficial veins of portions of the human body so that the veins may be punctured for the purpose of drawing blood or for the introduction of various medicinal materials.

2. Discussion of the Prior Art

The prior art includes various examples of constrictors or tourniquets which may be used to encircle a limb for various purposes, see, for example, U.S. Pat. Nos. 1,473,041, 1,607,996, 2,068,173, 2,258,720, 2,271,927, 2,519,712, 3,390,680, 3,760,803, 4,314,568 and 4,634,429. All of these patents are incorporated herein by reference.

U.S. Pat. No. 1,473,041 to Henderson discloses a tourniquet having pressure pads 3 formed thereon. The pressure pads exert pressure at localized locations to stop bleeding by exerting extra force on the area beneath them.

U.S. Pat. No. 1,607,996 to Morgenthaler shows a surgical tourniquet with a bead chain for holding a pressure element against the body. The pressure element is a locking arrangement for a portion of the bead chain so as to control the pressure applied by the tourniquet.

U.S. Pat. No. 2,068,173 to Galves discloses a device which protects an area of the body from contact and inhibits any pressure from being placed on the area by forming a raised surface above the area of the body to be protected.

U.S. Pat. No. 2,258,720 issued to Saighman discloses a tourniquet which has a wavy, irregular shaped surface to enhance the pressure placed on blood vessels to control the flow of bleeding.

U.S. Pat. No. 2,271,927 issued to Saighman discloses a tourniquet having raised pads which are designed to exert greater force on an area by extending below the encircling band of the tourniquet and are especially useful in flatter areas of the body.

U.S. Pat. No. 2,519,712 issued to Stegeman shows a tourniquet having a plurality of raised portions which are designed to act as fastening means, or locks, to position the tourniquet at a desired diameter.

U.S. Pat. No. 3,390,680 issued to Marcum discloses a tourniquet or constrictor device which can expand to a variety of diameter sizes.

U.S. Pat. No. 3,760,803 issued to Boothby shows a C-shaped spring element with pads which are adapted to press towards each other and thereby entrap a portion of flesh to facilitate injections.

U.S. Pat. No. 4,314,568 issued to Loving discloses a vascular stabilizing device having two body portions connected by a hinge and also connected by means of a tightening strap. By location of the body portions and hinge, a vein is positioned and squeezed in the space between the body portions.

U.S. Pat. No. 4,634,429 issued to Schoettley shows a one-piece spring device which is nonsymmetrical in nature to surround the limb and to squeeze a portion of the flesh in order to facilitate injecting into a vein.

A particular problem associated with various constrictors and tourniquets which have been used in the past is a requirement for ease of use which includes a need for rapid adjustment capability in order to accommodate limbs of different proportions and a need for a device which can be quickly and easily applied and released with only one hand, and which does not unnecessarily constrict the blood flow through the vessels that are sought to be found.

OBJECTS AND SUMMARY OF THE INVENTION

It is an object of this invention to provide a vein spotter which has an improved capability for distending superficial veins of the human body.

It is another object of this invention to provide a vein spotter which can easily be applied to an arm or leg and adjusted by a person using only one hand.

It is still another object of this invention to provide a vein spotter which effectively stabilizes the superficial veins, thereby facilitating the accurate use of a syringe.

It is a further object of this invention to provide a vein spotter which is easily adjustable, facilitating use on the arms and legs of a broad range of human physiques.

It is still a further object of this invention to provide a vein spotter which is relatively comfortable for the patient.

It is yet a further object of this invention to provide a vein spotter which incorporates a flexible band and a plurality of protrusion members which bear on a limb and which are displaced from the site of the venipuncture thereby eliminating contamination and a consequent need for sterilization prior to reuse.

Still another object of this invention is to provide a vein spotter which includes protruding members adapted to press into the flesh which will be displaced by the presence of superficial veins so as to isolate the vein without unduly constricting the flow in the vein.

Still another object of this invention is to provide a vein spotter which includes protruding members which can be attached at various positions to be adapted for use with the vein spotter at different parts of the anatomy.

Another object of this invention is to provide a vein spotter which incorporates a plurality of protrusions which are free to move in relation to the flexible band so as to avoid pressing on the superficial veins in their area.

Yet another object of this invention is to provide a vein spotter which incorporates a plurality of protrusions which are fastened to the flexible band in a manner that allows them to be moved or removed for optimal formation of an array of protrusions on the flexible band.

All of the foregoing objects are achieved by the vein spotter of this invention. The vein spotter comprises a flexible band which is generally rectangular in configuration. A buckle is attached to one end of the flexible band and a first surface of the flexible band has a hook and pile Velcro-type fastener mounted thereon. The buckle is proportioned to accept the free end of the flexible band so that the flexible band can form a loop of any desired size, and the size of the loop can be maintained by the hook and pile fastener.

The second surface of the flexible band has a plurality of protrusion members mounted thereon. Each of the protrusion members includes a base portion which extends across the width of the flexible band and a plurality of projecting finger portions, each of which projects from the base portion. The projecting finger portions are inwardly directed relative to the loop formed by the flexible band. The protrusion members may be mounted to the second surface of the flexible band by means of coacting hook and pile surfaces mounted on the bottom of the base portion of the protrusion member and the second surface of the flexible band.

In use, the projecting finger portions bear against the muscular portion of a limb which is encircled by the flexible band and push into the skin thereby causing the superficial veins to distend and facilitating the venipuncture procedure. The combination of the flexible band and projecting fingers allows for pivotal movement of the projecting fingers, so that the ends of the projecting fingers are free to move and be displaced by superficial veins, so that they will thereby provide a space that veins can be disposed without excessive pressure that would tend to collapse the vein and restrict blood flow through the vein.

DESCRIPTION OF THE DRAWINGS

Other important objects and functional and structural features of the invention will be apparent from the following detailed description taken in conjunction with the accompanying drawings, wherein.

DETAILED DESCRIPTION OF THE INVENTION

Figure 1:
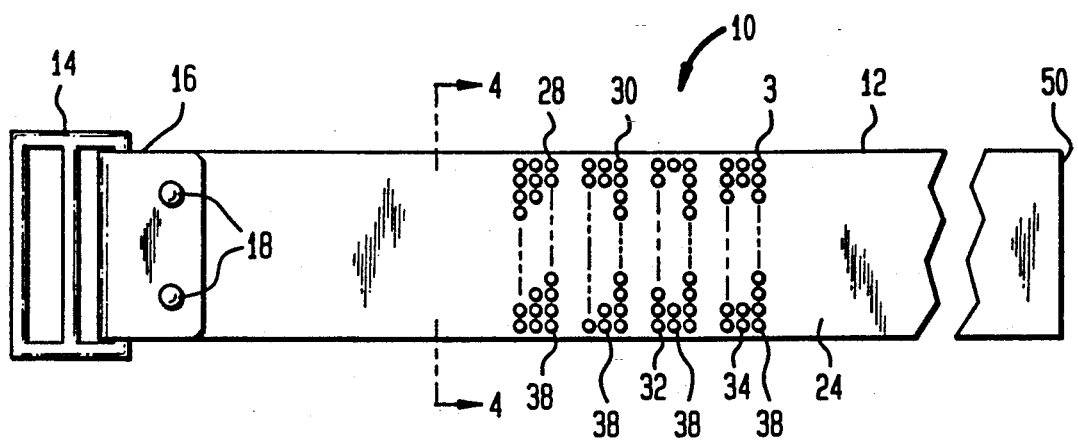
FIG. 1 is a top view of the vein spotter of this invention.
Figure 2:
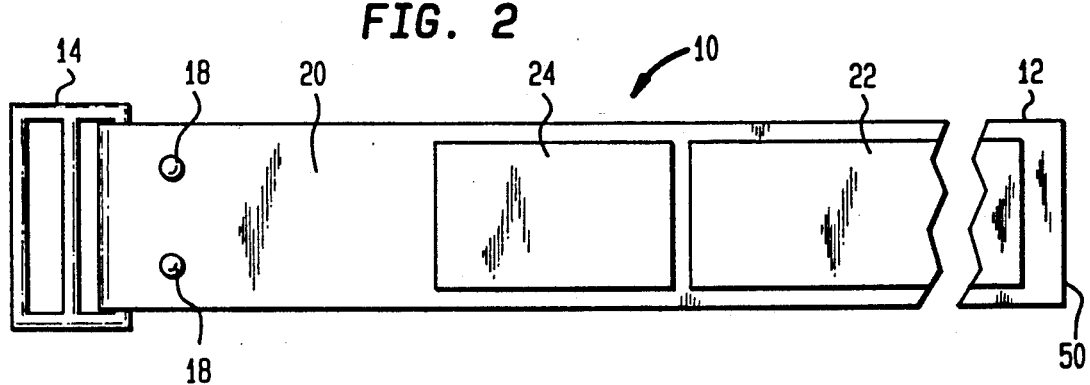
FIG. 2 is a bottom view of the vein spotter of this invention.

Referring to the drawings, and in particular FIGS. 1-4, the vein spotter 10 of this invention has a flexible band 12 which is generally rectangular in configuration. A buckle 14 is attached to the first end 16 of the band 12 by conventional means such as stitching or rivets 18. The first surface 20 of the band 12 has a panel of Velcro pile material 22 and a panel of Velcro hook material 24 mounted thereon, as is best shown in FIG. 2. The Velcro or hook and pile type fastener material panel 22 and the Velcro or hook and pile type fastener material panel 24 are attached to the band 12 using conventional attachment techniques such as stitching or rivets, which are not shown.

The second surface 26 of the band 12 has a plurality of protrusion members 28, 30, 32, 34 mounted thereon. Each of the protrusion members 28, 30, 32, 34 includes a generally rectangular base portion 36 which extends across the width of the band 12 and a plurality of generally cylindrical and parallel projecting finger portions 38 which project from the base portion 36. The finger portions 38 are disposed in a closely spaced array of three rows on each of the base portions 36 as is shown in FIG. 1. Each of the projecting finger portions 38 has a rounded end 40 which, during use, pushes into the skin of a patient's arm or leg to displace muscle and fat tissue thereby pushing the superficial veins upwards making it easier to find the veins.

Figure 3:
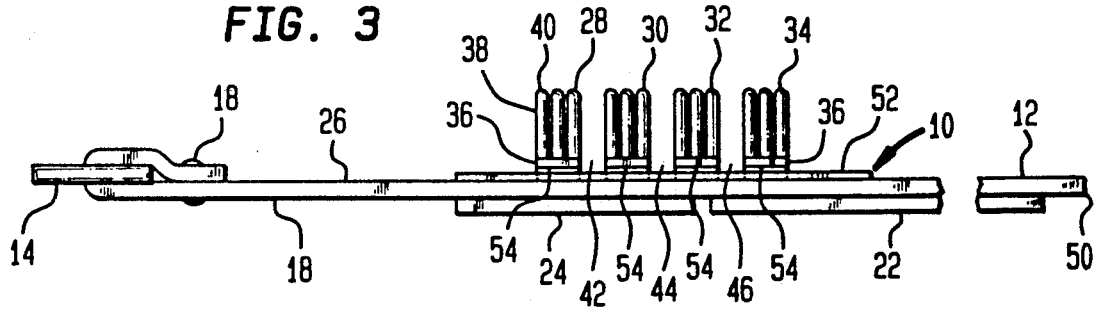
FIG. 3 is a side view of the vein spotter of this invention.
Figure 4:
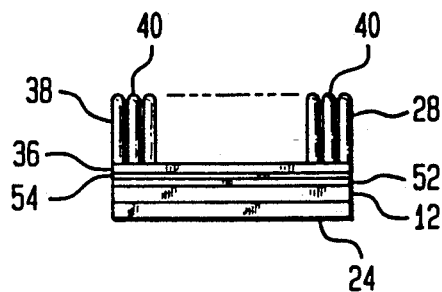
FIG. 4 is a cross-sectional view taken along the lines 4—4 of FIG. 1 drawn to an enlarged scale.

The protrusion members 28, 30, 32, 34 are spaced apart on the band 12 forming spaces 42, 44, 46 as is best shown in FIG. 3. During use, as the rounded ends 40 of the projecting finger portions 38 push into the limb of the patient, the flesh is squeezed upward into the spaces 42, 44, 46 between the protrusion members 28, 30, 32, 34 and is thereby held in a stabilized condition which facilitates the venipuncture procedure.

In the preferred embodiment of the invention, the band 12 may be constructed of a flexible fabric web material, and the protrusion members 28, 30, 32, 34 may be formed of a plastic material using a molding process.

Figure 5:
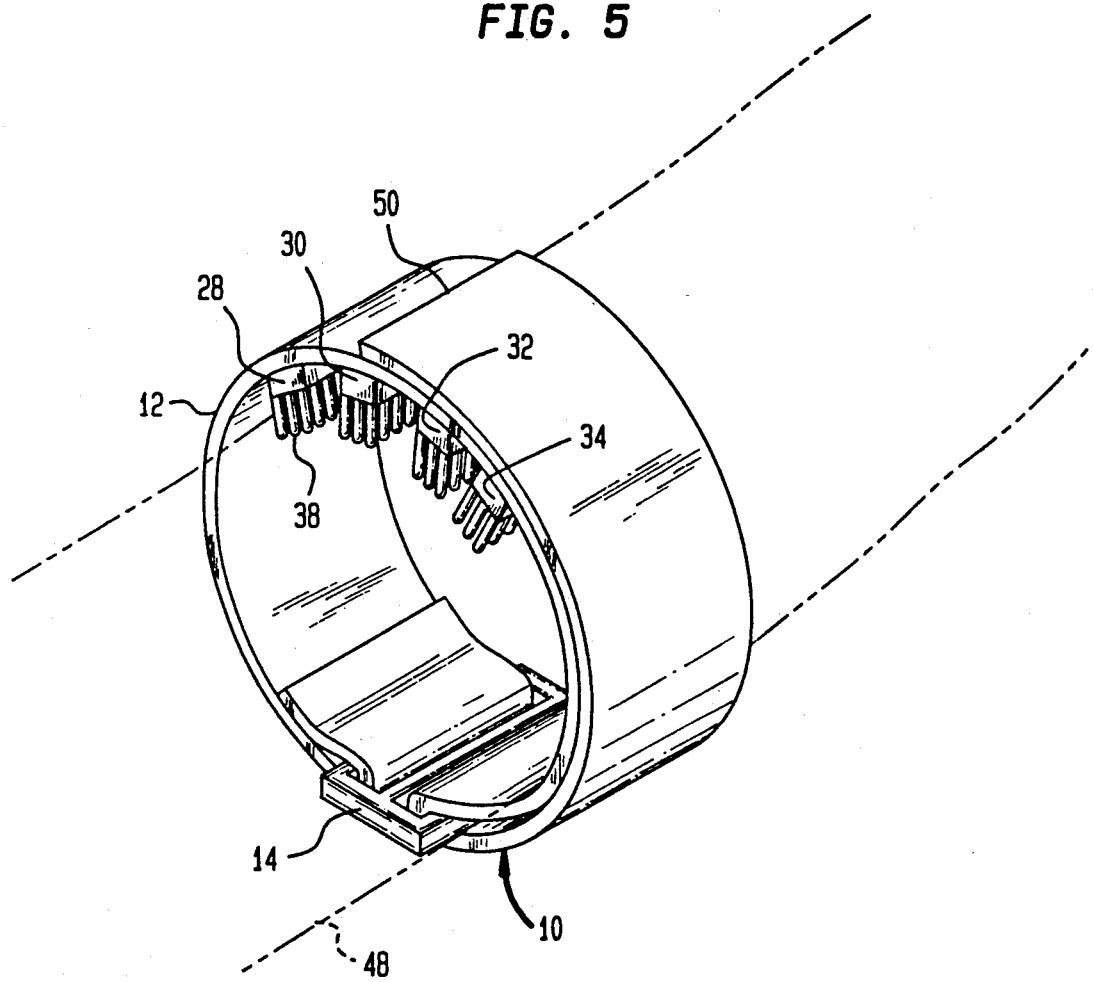
FIG. 5 is a perspective view of the vein spotter of this invention with the limb of a patient indicated in dashed lines.

As is shown in FIG. 5, during use, the band 12 is wrapped around the limb 48 of a patient, and the end 50 is passed through the buckle 14, tightened and then folded back against itself, so that the hook and pile panels 22, 24 coact to hold the band 12 securely in place. As the band 12 is tightened, the projecting finger portions 38 are pushed into the skin to displace the flesh. The superficial veins are displaced upwards thereby facilitating the venipuncture procedure.

The tightening of the band 12 on the limb 48 of the patient and the folding of the band in order to allow the hook and pile panels 22, 24 to coact may be easily accomplished with one hand allowing the physician to use his other hand to prepare and apply a syringe. The vein spotter 10 can be quickly and easily removed when the venipuncture procedure has been completed by pulling on the end 50 and separating the hook and pile panels 22, 24. The hook and pile panels 22, 24 allow the vein spotter 10 to be adjusted for a wide range of sizes of limbs.

The flexible band 12 accommodates itself to the contours of the limb 48 and provides the maximum degree of comfort for the patient while the plurality of rounded ends 40 on the projecting finger portions 38 push into the skin to displace the tissue, forcing the tissue into the spaces 42, 44, 46 between the protrusion members 28, 30, 32, 34 and causing the superficial veins to distend and become visible.

The height from end 40 of the finger portions 38, when combined with the height of the base portion 36, make the overall length to the end of the protrusion members much longer than the width of their support surface or base portion 36. Accordingly, the ends of the protrusion members will be able to move relative to the flexible band 12, and, therefore, will be displaced by a superficial vein which is relatively harder than the surrounding fat and muscle tissue. This compatibility of movement will, in effect, enable the protruding members to coact with each other to be self-seeking to find the superficial veins and provide a space between the protrusion members where the vein will not be subject compression.

Figure 6:
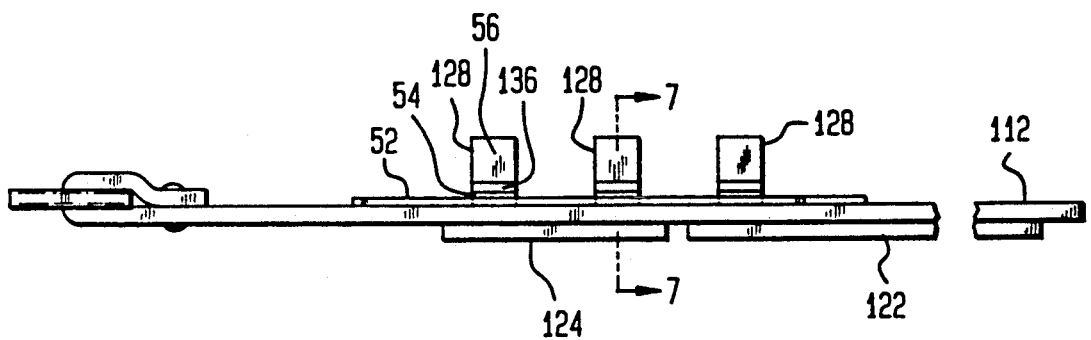
FIG. 6 is a view similar to FIG. 3 of another embodiment of the invention.
Figure 7:
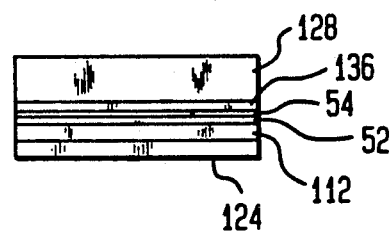
FIG. 7 is a cross sectional view taken along lines 7—7 of FIG. 6.

FIGS. 6 and 7 show another embodiment of the invention. Elements illustrated in FIGS. 6 and 7 which correspond to the elements described above with respect to FIGS. 1-5 have been designated by corresponding reference numerals increased by one hundred. The embodiments of FIGS. 6 and 7 are for use in the same manner as the embodiment of FIGS. 1-5 unless otherwise stated. In this embodiment, the protrusion members generally indicated at 128 have solid heads 56 and base members 136 which sit on a surface of fastening material 54 such as a hook and pile type fastener. This bottom surface 54 of the base 136 coacts with a surface 52 on the upper, inner, or first surface of the flexible band 112 and which is of the mating fabric of a hook and pile type fastener. Accordingly, the first surface 52 and the bottom surface 54 of the protruding members can be unfastened from each other and the protruding members moved anywhere along the fastening surface 52 on the first surface of the flexible band to be positioned as needed for coaction with each other in order to localize a surface vein. So, for example, the protruding members can be set at one space setting if the flexible band is to be placed around an arm, to find a vein in the arm, or another position setting can be used if the flexible band is to be placed around the thigh. Similarly, in the embodiment shown in FIGS. 3 and 4, the protrusion members 28 can include a hook and pile material 54 at the base portion 36 for coacting with another hook and pile material 52 disposed along the surface 26 of the band 12 for removably mounting the protrusion members to select positions along the band.

Additionally, different quantities of protruding members can be used and different shapes as appropriate. For example, in the initial embodiment, the protruding members include a plurality of fingers while the protruding members in the second embodiment include a solid head or other configurations.

The foregoing specific embodiment of the instant invention as set forth in the specification herein is for illustrative purposes only. Various changes and modifications may be made within the spirit and scope of this invention.

We claim:

1. A vein spotter comprising:
a flexible band, having a length dimension, a width dimension, a first surface and a second surface;
a plurality of protrusion members, said protrusion members mounted on said first surface of said flexible band and disposed in a spaced relationship, each of said protrusion members comprising a base portion and a plurality of finger portions, each projecting from said base portion;
said finger portions are each generally cylindrical in configuration, and each of said finger portions has a rounded projecting end, and said finger portions on each protrusion member form a closely spaced array with the finger portions being substantially parallel to each other;
length adjusting means including a buckle member attached to said flexible band and capable of forming said flexible band into a loop of adjustable size, and coacting hook and pile fastener means mounted on said second surface of said flexible band with said buckle member mounted on said first end and with said buckle member proportioned to accept said second end of said flexible band, said protrusion members inwardly directed relative to said loop for the purpose of encircling a human limb and causing said protrusion members to bear against said limb thereby causing superficial veins to distend and become visible;
each of said protrusion members capable of displacement relative to the adjacent protrusion members to enable accommodation of superficial veins between adjacent protrusion members.

2. A vein spotter comprising:
a flexible band, having a length dimension, a width dimension, a first surface and a second surface;
a plurality of protrusion members, said protrusion members mounted on said first surface of said flexible band and disposed in a spaced relationship, each of said protrusion members comprising a base portion and a plurality of finger portions, each projecting from said base portion;
a layer of hook and pile material disposed on said first surface;
each of said base portions of said protrusion members having a bottom surface, with hook and pile material on said bottom surface adapted to coact with the hook and pile material on said first surface to secure said protrusion member to said flexible band;
said finger portions are each generally cylindrical in configuration, and each of said finger portions has a rounded projecting end, and said finger portions on each protrusion member form a closely spaced array with the finger portions being substantially parallel to each other;
length adjusting means including a buckle member attached to said flexible band and capable of forming said flexible band into a loop of adjustable size, and coacting hook and pile fastener means mounted on said second surface of said flexible band with said buckle member mounted on said first end and with said buckle member proportioned to accept said second end of said flexible band, said protrusion members inwardly directed relative to said loop for the purpose of encircling a human limb and causing said protrusion members to bear against said limb thereby causing superficial veins to distend and become visible;
each of said protrusion members capable of displacement relative to the adjacent protrusion members to enable accommodation of superficial veins between adjacent protrusion members.

3. A vein spotter comprising:
a flexible band, having a length dimension, a width dimension, a first surface and a second surface;
a plurality of protrusion members, with said plurality of protrusion members mounted on said first surface of said flexible band, with said protrusion members disposed in a spaced relationship, each of said protrusion members having a base portion attached to said flexible band and a plurality of finger portions that each project from said base portion;
length adjustment means mounted on said flexible band and capable of forming said flexible band into a loop of adjustable size, with said protrusion members inwardly directed relative to said loop for the purpose of encircling a human limb and causing said protrusion members to bear against said limb thereby causing superficial veins to distend and become visible.

4. A vein spotter according to claim 3 in which said protrusion members each extend across said width dimension of said flexible band.

5. A vein spotter according to claim 3 in which said length adjustment means comprises a buckle member attached to said flexible band.

6. A vein spotter according to claim 4 in which said length adjustment means further comprises coacting hook and pile fastener means mounted on said second surface of said flexible band.

7. A vein spotter according to claim 3 in which said finger portions are each generally cylindrical in configuration.

8. A vein spotter according to claim 3 in which each of said finger portions has a rounded projecting end.

9. A vein spotter according to claim 3 in which said finger portions on each protrusion member form a closely spaced array.

10. A vein spotter according to claim 3 in which said flexible band is formed of fabric.

11. A vein spotter according to claim 3 in which said protrusion members are each formed of a moldable plastic material.

12. A vein spotter according to claim 3 in which said finger portions are substantially parallel to each other.

13. A vein spotter according to claim 5 in which said flexible band includes a first end and a second end with said buckle member mounted on said first end of said flexible band and with said buckle member proportioned to accept said second end of said flexible band.

14. A vein spotter according to claim 3 further including
 one of a hook and pile type fastener positioned on said first surface;
 a mating fastener of another hook and pile type fastener positioned on the bottom of each said base portion;
 said one of a hook and pile type fastener coacting with said mating fastener to removably mount said base portion of said protrusion members to said first surface.

15. A vein spotter comprising:
 a flexible band having a length dimension, a width dimension, a first surface and a second surface;
 a layer of hook and pile material disposed on said first surface;
 a plurality of protrusion members, each of said protrusion members having: a base portion; a bottom surface; another hook and pile material disposed on said bottom surface and adapted to coact with said hook and pile material on said first surface to removably mount and position said protrusion members to said first surface of said flexible band in a spaced relationship; and
 length adjusting means mounted on said flexible band and capable of forming said flexible band into a loop of adjustable size, wherein said protrusion members are directed inwardly relative to said loop to encircle a human limb and case said protrusion members to bear against said limb such that superficial veins distend and become visible.

* * * * *